(12) United States Patent
Eisinger (10) Patent No.: US 11,382,630 B2
(45) Date of Patent: Jul. 12, 2022

(54) SURGICAL STAPLING DEVICE WITH TWO PART KNIFE ASSEMBLY

(71) Applicant: Covidien LP, Mansfield, MA (US)

(72) Inventor: Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 143 days.

(21) Appl. No.: 16/800,483

(22) Filed: Feb. 25, 2020

(65) Prior Publication Data
US 2021/0259692 A1 Aug. 26, 2021

(51) Int. Cl.
*A61B 17/072* (2006.01)
*A61B 17/115* (2006.01)
*A61B 17/00* (2006.01)

(52) U.S. Cl.
CPC ... *A61B 17/1155* (2013.01); *A61B 2017/0053* (2013.01); *A61B 2017/00477* (2013.01); *A61B 2017/07257* (2013.01); *A61B 2017/07271* (2013.01); *A61B 2017/07285* (2013.01)

(58) Field of Classification Search
CPC ...... A61B 2017/07285; A61B 17/1155; A61B 2017/07257
USPC ..................................................... 227/180.1
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev et al. | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A * | 9/1981 | Rothfuss ............. | A61B 17/115 227/175.3 |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |

(Continued)

FOREIGN PATENT DOCUMENTS

| CA | 908529 A | 8/1972 |
|---|---|---|
| CA | 2805365 A1 | 8/2013 |

(Continued)

OTHER PUBLICATIONS

European Search Report dated Jun. 28, 2021, issued in corresponding EP Application No. 21159082, 7 pages.

*Primary Examiner* — Gloria R Weeks (57) ABSTRACT

A stapling device is provided that includes a reload assembly and an anvil assembly. The anvil assembly supports a cut ring. The reload assembly includes a knife assembly that has a distal knife portion and a proximal knife portion that are separate from each other. The distal knife portion includes a cutting edge and is movable with the proximal knife portion from a retracted position to an advanced position into engagement with the cut ring. In the advanced position, the distal knife portion is retained by the cut ring to shield the cutting edge of the distal knife portion.

21 Claims, 8 Drawing Sheets

(56) References Cited

U.S. PATENT DOCUMENTS

| | | | |
|---|---|---|---|
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A * | 3/1986 | Conta | A61B 17/115 227/179.1 |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A * | 10/1988 | Green | A61B 17/115 227/19 |
| 4,817,847 A | 4/1989 | Redtenbacher et al. | |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A * | 9/1990 | Lipatov | A61B 17/115 227/180.1 |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A * | 12/1993 | Grant | A61B 17/115 227/179.1 |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A * | 12/1996 | Schnut | A61B 17/115 227/175.1 |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 * | 2/2001 | Bittner | A61B 17/1114 227/19 |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |

(56) References Cited

U.S. PATENT DOCUMENTS

| | | | |
|---|---|---|---|
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 * | 1/2007 | Milliman ............ A61B 17/1114 |
| | | | 227/175.1 |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 * | 4/2008 | Milliman ............ A61B 17/068 |
| | | | 227/175.1 |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 * | 8/2010 | Chen ............... A61B 17/115 |
| | | | 227/180.1 |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | | |
|---|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,573,464 B2 * | 11/2013 | Nalagatla ........... A61B 17/1155 |
| | | 227/179.1 |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,421,013 B2 * | 8/2016 | Patel .................... A61B 17/068 |
| 10,405,864 B2 * | 9/2019 | Zhan .................. A61B 17/1155 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0278346 A1 * | 11/2011 | Hull .................. A61B 17/1155 |
| | | 227/180.1 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0292368 A1 * | 11/2012 | Nalagatla ............. H04B 7/0682 |
| | | 227/175.2 |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 * | 3/2013 | Giacomantonio .. A61B 17/1114 |
| | | 227/180.1 |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |

(56) References Cited

U.S. PATENT DOCUMENTS

| | | | |
|---|---|---|---|
| 2013/0153633 A1 | 6/2013 | Casasanta, Jr. et al. | |
| 2013/0153634 A1 | 6/2013 | Carter et al. | |
| 2013/0153638 A1 | 6/2013 | Carter et al. | |
| 2013/0153639 A1 | 6/2013 | Hodgkinson et al. | |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181035 A1 | 7/2013 | Milliman | |
| 2013/0181036 A1 | 7/2013 | Olson et al. | |
| 2013/0186930 A1 | 7/2013 | Wenchell et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193191 A1 | 8/2013 | Stevenson et al. | |
| 2013/0193192 A1 | 8/2013 | Casasanta, Jr. et al. | |
| 2013/0200131 A1 | 8/2013 | Racenet et al. | |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0277411 A1 | 10/2013 | Hodgkinson et al. | |
| 2013/0277412 A1 | 10/2013 | Gresham et al. | |
| 2013/0284792 A1 | 10/2013 | Ma | |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306701 A1 | 11/2013 | Olson | |
| 2013/0306707 A1 | 11/2013 | Viola et al. | |
| 2014/0008413 A1 | 1/2014 | Williams | |
| 2014/0012317 A1 | 1/2014 | Orban et al. | |
| 2015/0173757 A1* | 6/2015 | Williams | A61B 17/072 227/180.1 |
| 2016/0000428 A1* | 1/2016 | Scirica | A61B 1/00089 227/180.1 |
| 2016/0143641 A1 | 5/2016 | Sapienza et al. | |
| 2016/0157856 A1* | 6/2016 | Williams | A61B 17/1155 227/175.1 |
| 2016/0174988 A1 | 6/2016 | D'Agostino et al. | |
| 2016/0302792 A1 | 10/2016 | Motai | |
| 2018/0233850 A1* | 8/2018 | Penna | A61B 17/1155 |
| 2020/0138441 A1* | 5/2020 | Sgroi, Jr. | A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524655 A1 | 11/2012 |
| EP | 2524656 A2 | 11/2012 |
| EP | 2754398 A2 | 7/2014 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

SURGICAL STAPLING DEVICE WITH TWO PART KNIFE ASSEMBLY

FIELD

This disclosure is generally related to stapling devices and, more particularly, to circular stapling devices including a knife to cut tissue.

BACKGROUND

Circular stapling devices typically include a shell or reload assembly that includes a staple cartridge that supports one or more annular rows of staples, a staple pusher for ejecting the staples from the staple cartridge, and an annular knife that is positioned radially inward of the annular rows of staples for cutting tissue. The knife can be movable simultaneously with the staple pusher or independently of the staple pusher to cut tissue during a surgical procedure, e.g., an anastomosis procedure.

During an anastomosis procedure, two tubular sections of tissue are attached to one another and the sections of tissue within the annular knife are cored with the knife to define a hollow passage between the joined tubular sections. Generally, a tissue donut remains within the annular knife of the reload assembly after the tissue sections have been cut. When the reload assembly is removed from a patient, the tissue donut is removed from within the knife by the clinician.

After a circular stapling device is actuated to cut tissue during an anastomosis procedure, the knife is moved from an advanced position to a retracted position in which a cutting edge of the knife is recessed and shielded within a shell housing of the reload assembly. During removal of the tissue donut from within the annular knife, the cutting edge of the knife is pulled in a direction back towards the advanced position and may become exposed.

SUMMARY

The techniques of this disclosure generally relate to circular stapling devices having a knife to cut tissue.

One aspect of the disclosure is directed to a reload assembly that includes a shell housing, a staple cartridge, a staple pushing member, a knife carrier, and a knife assembly. The shell housing defines a cavity and has a proximal portion and a distal portion. The staple cartridge is supported on the distal portion of the shell housing and supports a plurality of staples. The staple pushing member is movable within the shell housing between an advanced position and a retracted position to eject the plurality of staples from the staple cartridge. The staple pushing member defines a longitudinal bore. The knife carrier is supported within the longitudinal bore of the staple pushing member and is movable between retracted and advanced positions within the shell housing. The knife assembly includes a distal knife portion and a proximal knife portion. The proximal knife portion is secured to the knife carrier and is movable with the knife carrier as the knife carrier is moved between its retracted and advanced positions. The distal knife portion is in abutting relation with the proximal knife portion, such that the knife carrier is movable from its advanced position to its retracted position independently of the distal knife portion.

Another aspect of the disclosure is directed to a stapling device including a handle assembly, an adaptor assembly, an anvil assembly, and a reload assembly. The adaptor assembly extends from the handle assembly and has a distal end portion. The anvil assembly includes a cut ring. The reload assembly is supported on the distal end portion of the adaptor assembly and includes a shell housing, a staple cartridge, a staple pushing member, a knife carrier, and a knife assembly. The shell housing defines a cavity and has a proximal portion and a distal portion. The staple cartridge is supported on the distal portion of the shell housing and supports a plurality of staples. The staple pushing member is movable within the shell housing between an advanced position and a retracted position to eject the plurality of staples from the staple cartridge. The staple pushing member defines a longitudinal bore. The knife carrier is supported within the longitudinal bore of the staple pushing member. The knife carrier is movable between retracted and advanced positions within the shell housing. The knife assembly includes a distal knife portion and a proximal knife portion. The proximal knife portion is secured to the knife carrier and is movable with the knife carrier between retracted and advanced positions as the knife carrier is moved between its retracted and advanced positions. The distal knife portion is in abutting relation with the proximal knife portion such that movement of the proximal knife portion to its advanced position moves the distal knife portion to an advanced position. The knife carrier is movable from its advanced position to its retracted position independently of the distal knife portion.

Another aspect of the disclosure is directed to a reload assembly including a shell housing, a staple cartridge, a staple pushing member, and a knife assembly. The shell housing defines a cavity and has a proximal portion and a distal portion. The staple cartridge is supported on the distal portion of the shell housing and supports a plurality of staples. The staple pushing member is movable within the shell housing between an advanced position and a retracted position to eject the plurality of staples from the staple cartridge. The staple pushing member defines a longitudinal bore. The knife assembly includes a distal knife portion and a proximal knife portion. The distal knife portion is in abutting relation with the proximal knife portion such that the proximal knife portion is movable from its advanced position to its retracted position independently of the distal knife portion.

In aspects of the disclosure, the proximal and distal knife portions are annular.

In some aspects of the disclosure, the proximal knife portion has a first diameter and the distal knife portion has a second diameter, wherein the first diameter is equal to the second diameter.

In certain aspects of the disclosure, the distal knife portion includes an annular cutting edge.

In aspects of the disclosure, the knife carrier includes a distal body portion that includes distal extensions that extend along the knife assembly to maintain alignment of the proximal and distal knife portions.

In some aspects of the disclosure, the distal knife portion includes an opening positioned adjacent and proximal to the annular cutting edge.

In aspects of the disclosure, the opening is dimensioned to receive a retention member of an anvil assembly.

In certain aspects of the disclosure, the reload assembly includes a coupling mechanism that is adapted to secure the reload assembly to a stapling device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Various aspects and features of the disclosure are described with reference to the drawings wherein like numerals designate identical or corresponding elements in each of the several views and.

DETAILED DESCRIPTION

The disclosed reload assembly in association with a surgical stapling device will now be described in detail with reference to the drawings in which like reference numerals designate identical or corresponding elements in each of the several views. However, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician during use of the device in its customary manner, while the term "distal" is used generally to refer to that portion of the device that is farther from the clinician during use of the device in its customary manner. Further, the term "clinician" is used generally to refer to medical personnel including doctors, nurses, and support personnel.

Figure 1:
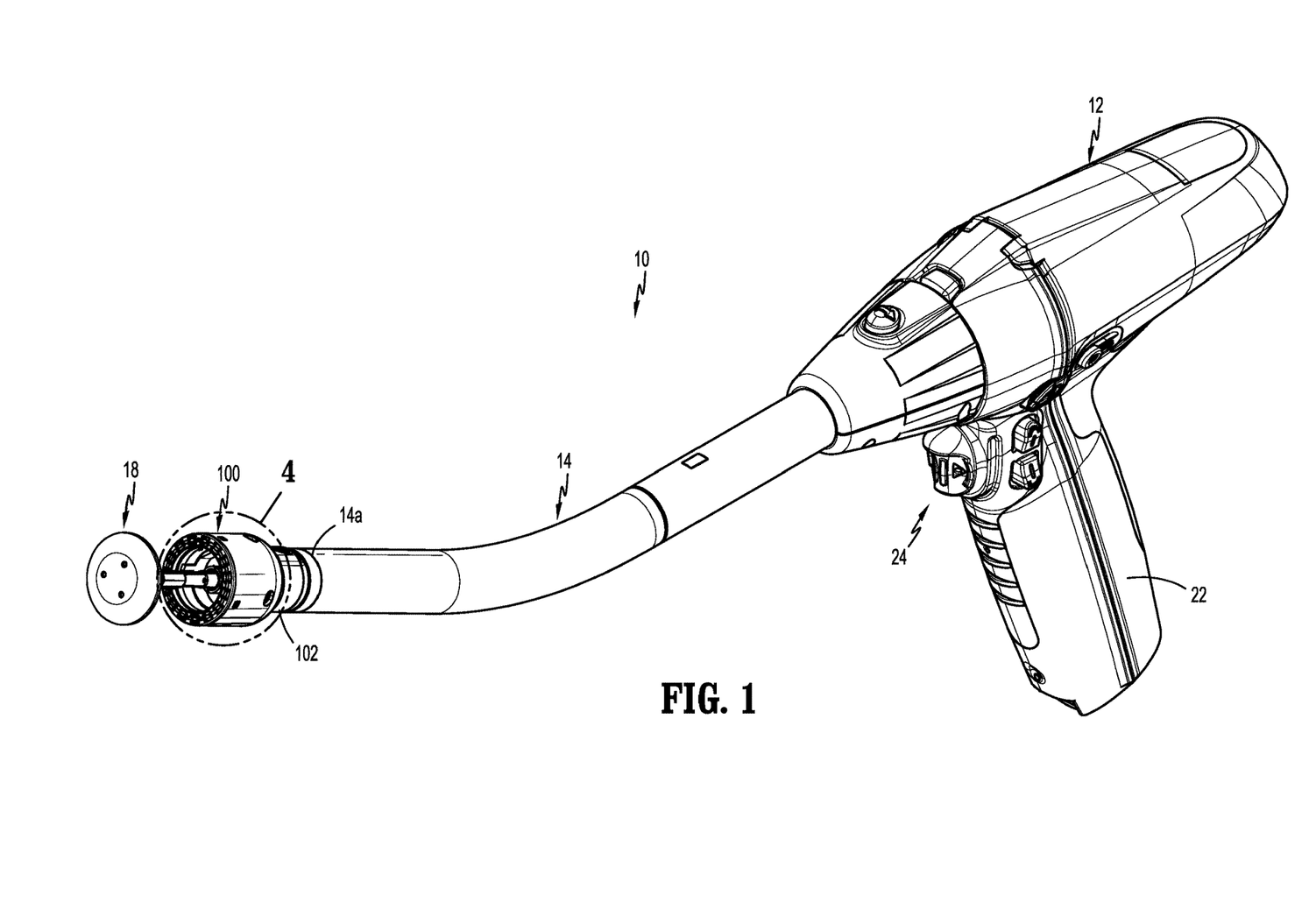
FIG. 1 is a side perspective view of a surgical stapling device including a tool assembly having a reload assembly in accordance with aspects of the disclosure.

FIG. 1 illustrates a circular stapling device 10 including a reload assembly in accordance with aspects of the disclosure shown generally as a reload assembly 100. The circular stapling device 10 includes a handle assembly 12, an elongate body or adaptor assembly 14, the reload assembly 100, and an anvil assembly 18 that is supported for movement in relation to the reload assembly 100 between a spaced position (FIG. 5) and a clamped position (FIG. 6). The reload assembly 100 includes a proximal portion 102 that is releasably coupled to a distal portion of the adaptor assembly 14 and the adaptor assembly 14 includes a proximal portion that is releasably coupled to the handle assembly 12. The handle assembly 12 includes a stationary grip 22 that supports actuation buttons 24 for controlling operation of various functions of the circular stapling device 10 including approximation of the reload assembly 100 and anvil assembly 18, firing of staples from the reload assembly 100, and cutting or coring of tissue as described in further detail below. It is envisioned that the handle assembly 12, the adaptor assembly 14, and/or the reload assembly could be fixedly secured to each other.

The circular stapling device 10 is illustrated as an electrically powered stapling device including an electrically powered handle assembly 12 that may support one or more batteries (not shown). The adaptor assembly 14 translates power from the handle assembly 12 to the reload and anvil assemblies 100, 18, respectively, to staple and cut tissue. Examples of electrically powered stapling devices can be found in U.S. Pat. Nos. 9,055,943, 9,023,014, and U.S. Publication Nos. 2018/0125495, and 2017/0340351. Alternately, it is envisioned that aspects of the reload assembly 100 disclosed herein could also be incorporated into a manually powered stapling device such as disclosed in, e.g., U.S. Pat. No. 7,303,106 (the '106 patent), or a stapling device that is configured for use with a robotic system as disclosed in, e.g., U.S. Pat. No. 9,962,159, that does not include a handle assembly.

Figure 2:
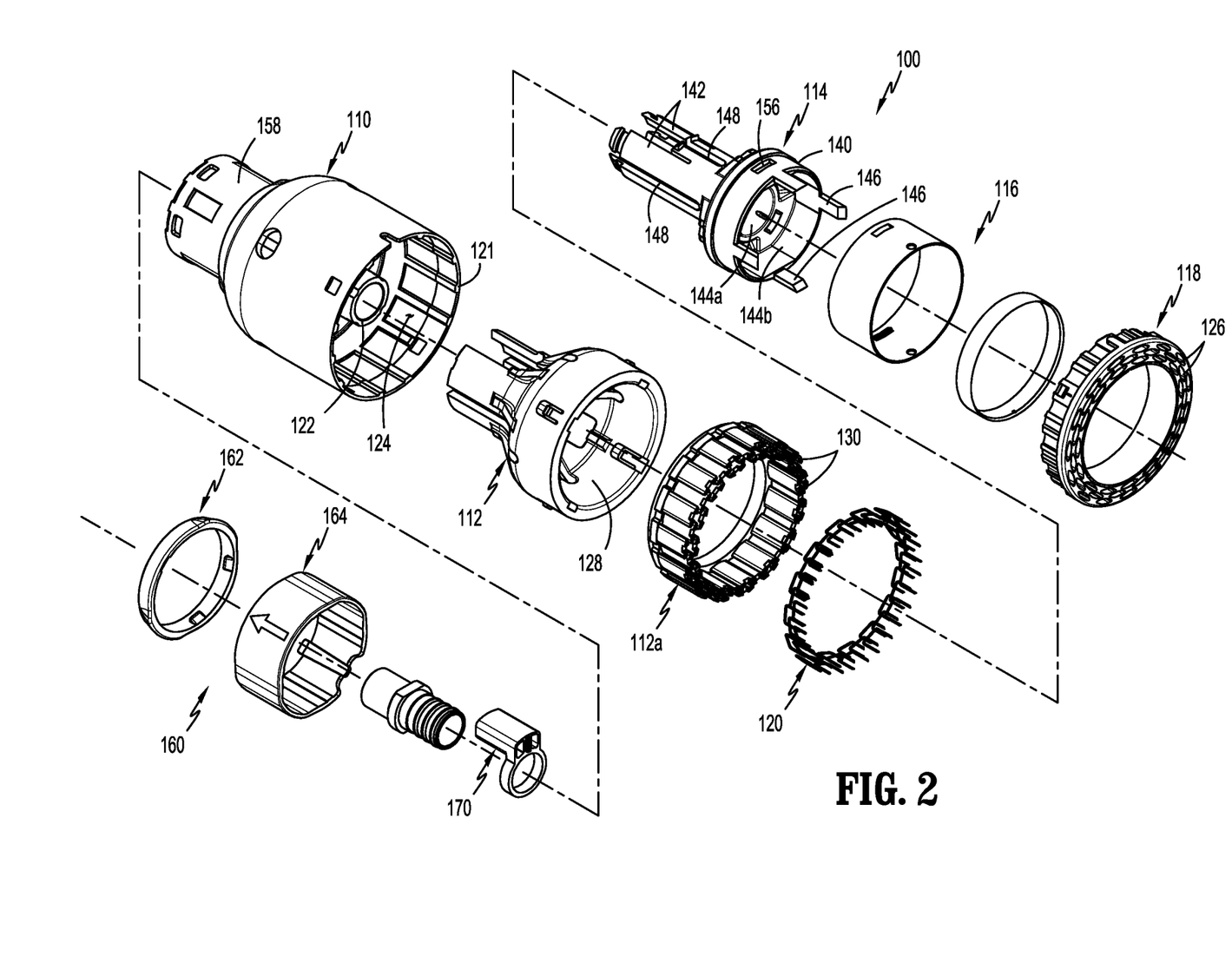
FIG. 2 is an exploded side perspective view of the reload assembly shown in FIG. 1.

FIG. 2 illustrates an exploded view of the reload assembly 100 which includes a shell housing 110, a staple actuator 112, a staple pushing member 112a, a knife carrier 114, an annular knife assembly 116 supported on the knife carrier 114, a staple cartridge 118, and a plurality of staples 120 supported within the staple cartridge 118. The shell housing 110 includes an outer housing portion 121 and an inner housing portion 122 that are spaced from each other to define an annular cavity 124 (FIG. 5) positioned between the outer and inner housing portions 121 and 122. The staple actuator 112 and the staple pushing member 112a are movable within the annular cavity 124 of the shell housing 110 from a retracted position to an advanced position to eject the staples 120 from the staple cartridge 118 as described in further detail below.

The staple cartridge 118 is annular and defines annular rows of staple pockets 126. Each of the staple pockets 126 supports one of the staples 120. The staple actuator 112 and the staple pushing member 112a together define a longitudinal through bore 128 (FIG. 5) that receives the knife carrier 114. The staple actuator 112 has a distal portion that abuts a proximal portion of the staple pushing member 112a such that distal movement of the staple actuator 112 within the shell housing 110 causes distal movement of the staple pushing member 112a within the shell housing 110. The staple pushing member 112a of the reload assembly 100 has a plurality of fingers 130. Each of the plurality of fingers 130 is received within a respective one of the staple pockets 126 of the staple cartridge 118 and is movable through the respective staple pocket 126 to eject the staples 120 from the staple pockets 126 when the staple pushing member 112a is moved from its retracted position to its advanced position within the shell housing 110.

The knife carrier 114 is received within the longitudinal through bore 128 of the staple actuator 112 and includes a distal body portion 140 and a plurality of spaced longitudinally extending proximal body portions 142. The distal body portion 140 and the proximal body portions 142 define a stepped central bore having a proximal portion 144a and a distal portion 144b. The proximal portion 144a of the stepped central bore of the knife carrier 114 slidably receives the inner housing portion 122 of the shell housing 110 such that the knife carrier 114 is movable within the staple actuator 112 about the inner housing portion 122 of the shell housing 110 between a retracted position (FIG. 5) and an advanced position (FIG. 6). The distal body portion 140 of the knife carrier 114 includes a plurality of longitudinal extensions 146 that are described in further detail below. The proximal body portions 142 of the knife carrier 114 defines slots 148 that receive guide portions (not shown) of the shell housing 110 to limit the knife carrier 114 to longitudinal movement within the shell housing 110.

Figure 3:
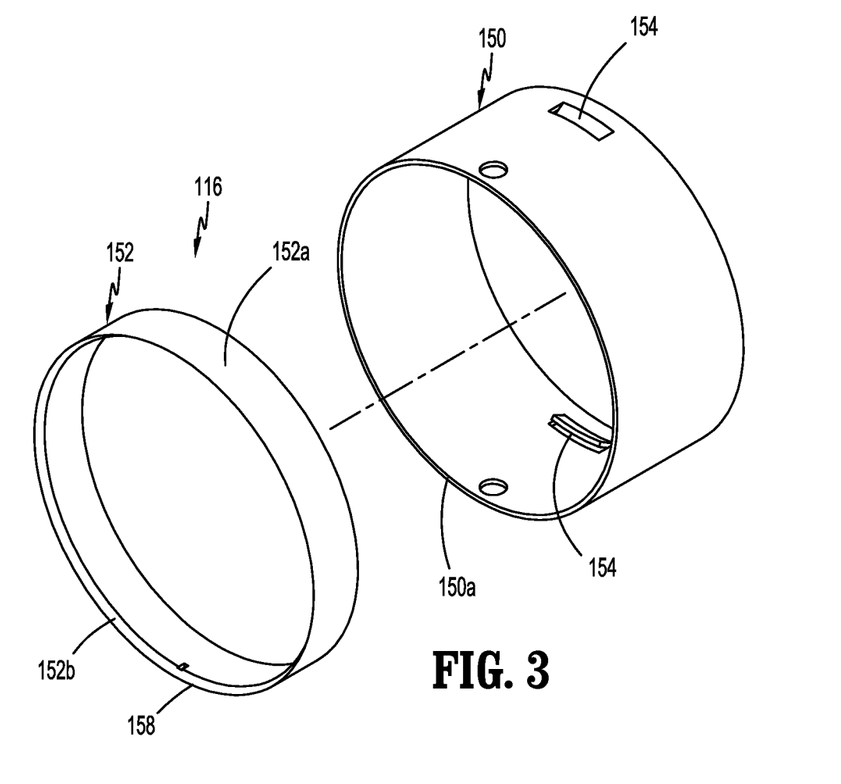
FIG. 3 is a side perspective view of a two part knife assembly of the reload assembly shown in FIG. 2.
Figure 4:
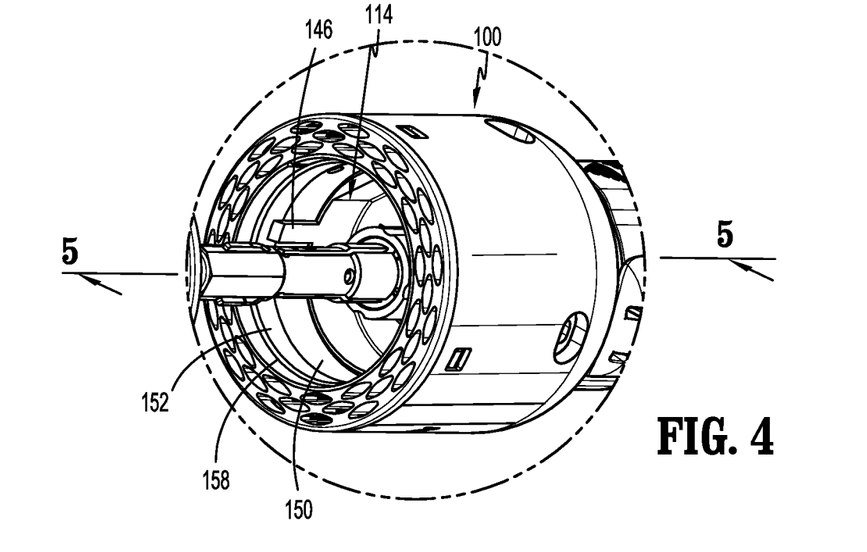
FIG. 4 is an enlarged view of the indicated area of detail shown in FIG. 1.

FIGS. 3 and 4 illustrate the annular knife assembly 116 of the reload assembly 100 which includes a proximal knife portion 150 and a distal knife portion 152. The proximal knife portion 150 is annular and includes inwardly extending tangs 154 that are received within recesses 156 (FIG. 2) defined within the distal body portion 140 of the knife carrier 114 to secure the proximal knife portion 150 about the knife carrier 114. Alternately, other techniques can be used to secure the proximal knife portion 150 to the knife carrier 114. The distal knife portion 152 of the knife assembly 116 is also annular and includes a proximal end 152a and a distal end 152b. The distal knife portion 152 has a diameter that is substantially equal to the diameter of the proximal knife portion 150 such that the proximal end 152a of the distal knife portion 152 is positioned in abutting relation to a distal end 150a of the proximal knife portion 150. The distal end 152b of the distal knife portion 152 defines an annular cutting edge 158. The distal knife portion 152 of the knife assembly 116 is received about the longitudinal extensions 146 (FIG. 4) of the knife carrier 114. Engagement between the distal knife portion 152 of the knife assembly 116 and the longitudinal extensions 146 of the knife carrier 114 maintains alignment between the distal knife portion 152 and the proximal knife portion 150 (FIG. 4).

FIG. 2 illustrates a proximal portion 159 of the shell housing 110 that supports a coupling mechanism 160 (FIG. 3). The coupling mechanism 160 is operable to releasably couple the reload assembly 100 to the adaptor assembly 14 of the stapling device 10 (FIG. 1) to facilitate replacement of the reload assembly 100 and reuse of the stapling device 10. The coupling mechanism 160 includes a retaining member 162 and a coupling member 164. The coupling member 164 is received about the proximal portion 158 of the shell housing 110 and is configured to engage the distal portion 14a (FIG. 1) of the adaptor assembly 14 to couple the adaptor assembly 14 to the reload assembly 100. It is envisioned that other coupling mechanisms can be used to secure the reload assembly 100 to the adaptor 14.

The reload assembly 100 may include an e-prom holder 170 (FIG. 2) that is supported on the shell housing 110 to support an e-prom (not shown). As is known in the art, an e-prom communicates with the adaptor assembly 14 to provide information to the adaptor assembly 14 and the handle assembly 12 related to characteristics of the reload assembly 10.

Figure 5:
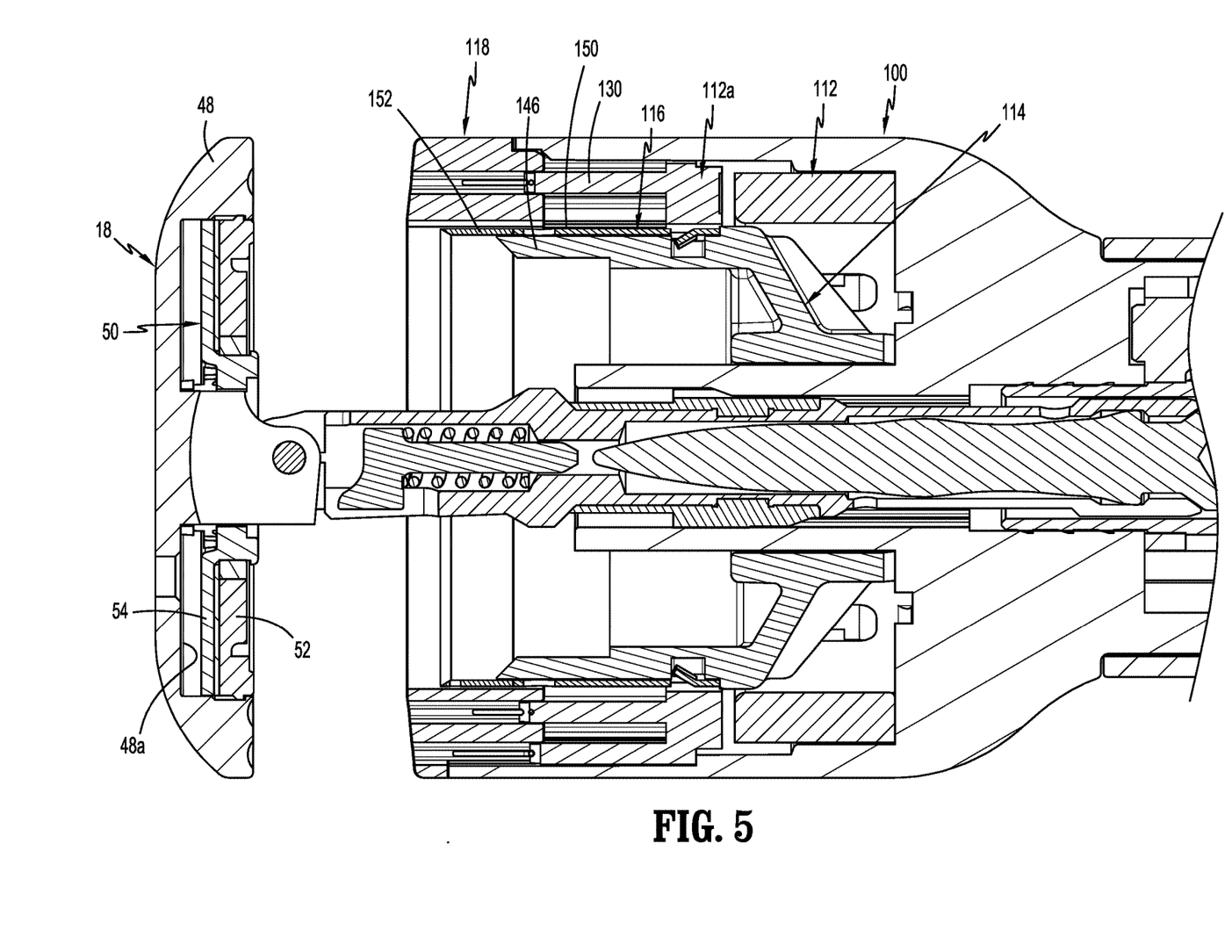
FIG. 5 is a cross-sectional view taken along section line 5-5 of FIG. 4 with the tool assembly in an unclamped, pre-fired position.
Figure 6:
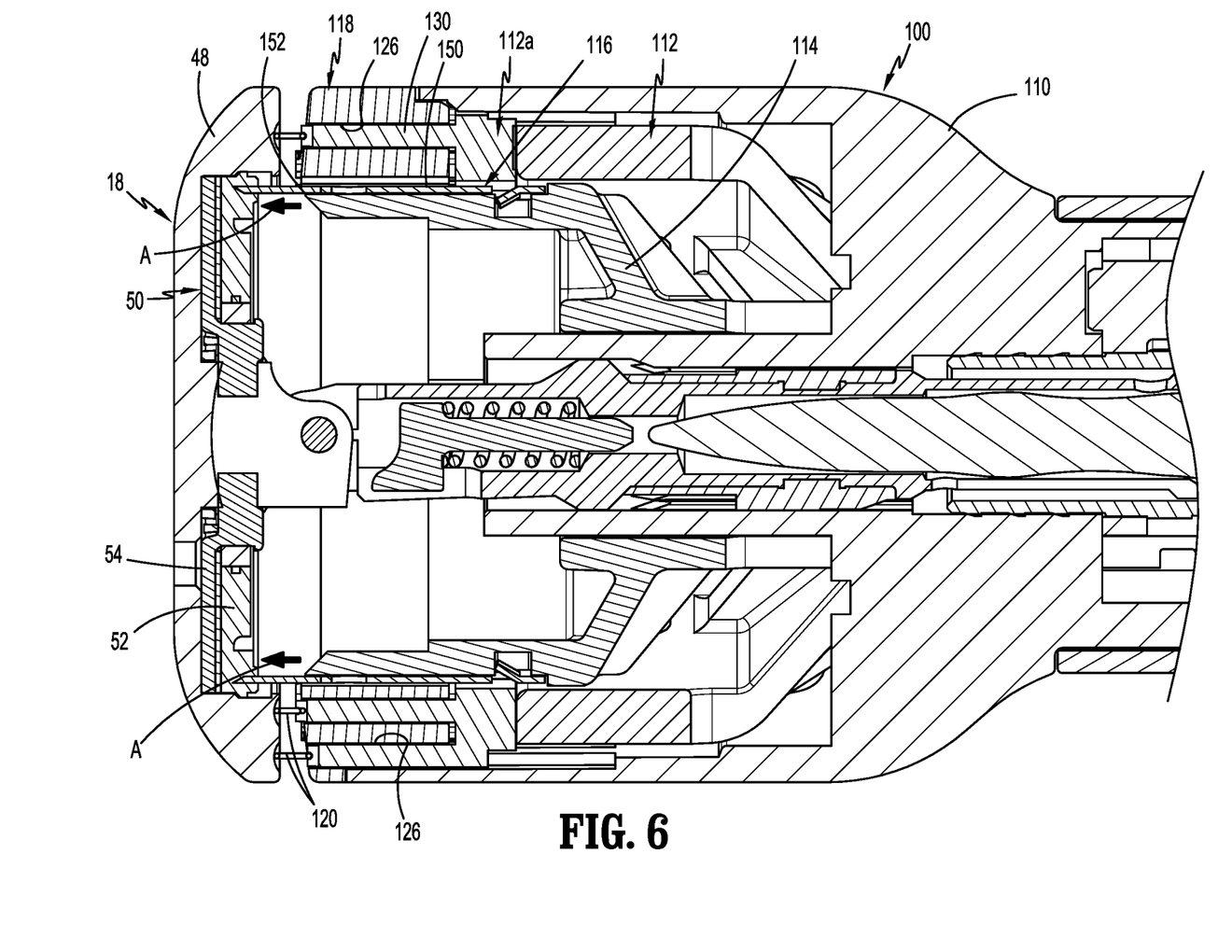
FIG. 6 is a cross-sectional view taken along section line 5-5 of FIG. 4 with the tool assembly in a clamped, fired, and advanced position.

FIG. 5 illustrates the reload assembly 100 and the anvil assembly 18 in a pre-fired, unclamped position. In this position, the staple actuator 112, the staple pushing member 112a, the knife carrier 114, and the annular knife assembly 116 are in their retracted positions with the proximal knife portion 150 secured to the knife carrier 114 and the distal knife portion 152 positioned in abutting relation with the proximal knife portion 150 between the longitudinal extensions 146 of the knife carrier 114 and an inner wall of the staple cartridge 118.

The anvil assembly 18 includes housing 48 and a cut ring assembly 50 that is received within a cavity 48a defined by the housing 48 and includes a compliant cut ring 52 and a rigid backup plate 54. In aspects of the disclosure, the cut ring assembly 50 is movable within the cavity 48a from a retracted position to an advanced position in response to being engaged by the knife assembly 116 as described below. The compliant cut ring 52 is formed of a material that can be penetrated by the knife assembly 116 to facilitate the cutting of tissue clamped between the anvil assembly 18 and the staple cartridge 118 of the reload assembly 100.

FIG. 6 illustrates the reload assembly 100 and the anvil assembly 18 in a clamped and fired position. In this position, the staple actuator 112, the staple pushing member 112a, the knife carrier 114, and the annular knife assembly 116 have been moved in the direction indicated by arrow "A" to their advanced positions. As illustrated, in the advanced position of the staple pushing member 112a, the fingers 130 of the staple pushing member 112a are received within the staple pockets 126 of the staple cartridge 118 to drive the staples 120 from the staple pockets 126 and form the staples against the anvil assembly 18. In the advanced position of the knife assembly 116, the distal knife portion 152 of the knife assembly 116 is engaged with and penetrates the compliant cut ring 52.

Figure 7:
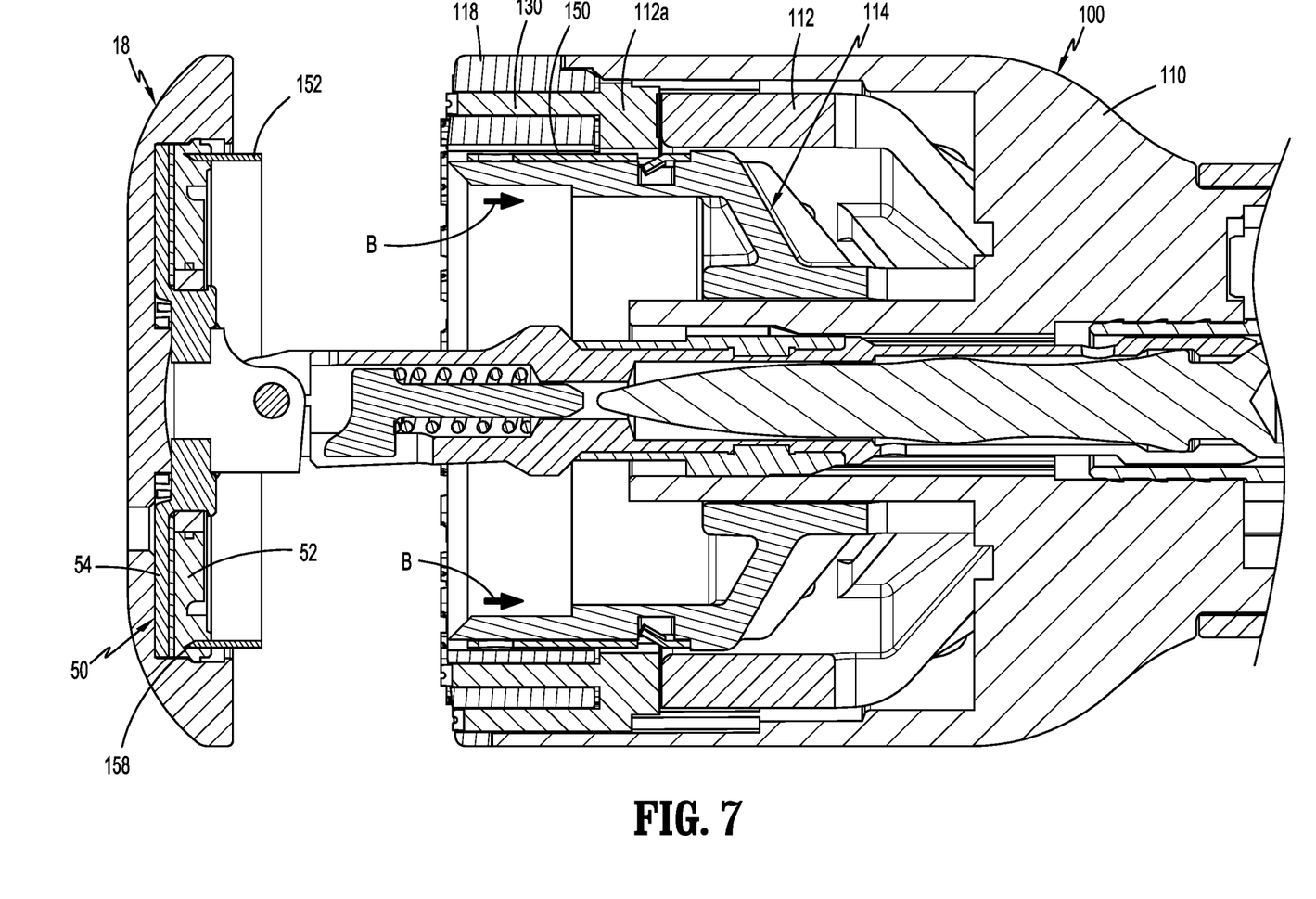
FIG. 7 is a cross-sectional view taken along section line 5-5 of FIG. 4 with the tool assembly in a clamped, fired, and retracted position with the knife fractured into two parts.
Figure 8:
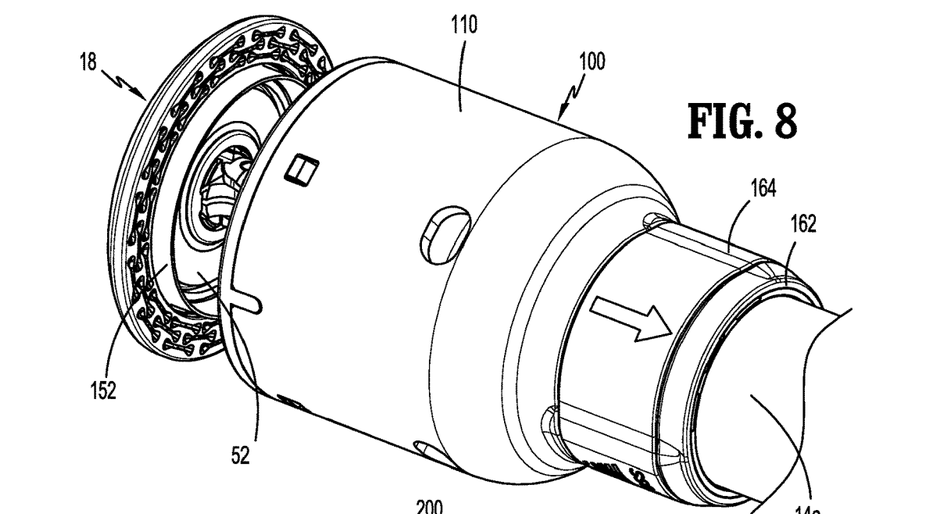
FIG. 8 is a side perspective view of the tool assembly shown in FIG. 1 with the tool assembly in a clamped, fired, and retracted position with the knife fractured into two parts.

FIGS. 7 and 8 illustrate the reload assembly 100 and the anvil assembly 18 in a post-fired unclamped position. In this position, the staple actuator 112 and the knife carrier 114 are returned in the direction indicated by arrows "B" to their retracted positions. Since the staple pushing member 112a and the staple actuator 112 are only in abutting relation, the staple pushing member 112a remains in an advanced position with the fingers 130 received within the staple pockets 126 of the staple cartridge 118. Similarly, since the proximal knife portion 150 is only in abutting relation to the distal knife portion 152 of the knife assembly 116, the distal knife portion 152 remains in its advanced position engaged with the compliant cut ring 52 when the knife carrier 114 and proximal knife portion 150 return to their retracted position. It is noted frictional engagement between the distal knife portion 152 and the compliant cut ring 52 of the cut ring assembly 50 retains the distal knife portion 152 in its advanced position with the annular cutting edge 158 of the distal knife portion 152 of the knife assembly 116 buried within and shielded by the compliant cut ring 52.

FIGS. 9-12 illustrate another reload assembly according to other aspects of the disclosure shown generally as reload assembly 200. The reload assembly 200 is substantially identical to reload assembly 100 except that the distal knife portion 252 of the knife assembly 216 includes a recess or opening 260. The anvil assembly 18 also includes a cut ring assembly 250 including a compliant cut ring 352 that defines a bore 362 that is positioned to receive the distal knife portion 252 of the knife assembly 216 when the knife assembly 216 is moved from its retracted position (FIG. 9) to its advanced position. The compliant cut ring 352 includes a retention member 364 that extends into the bore 362 and is received within the opening 260 in the distal knife portion 252 when the knife assembly 216 is in its advanced position (FIG. 11) and the distal knife portion 252 is positioned within the bore 362.

Figure 9:
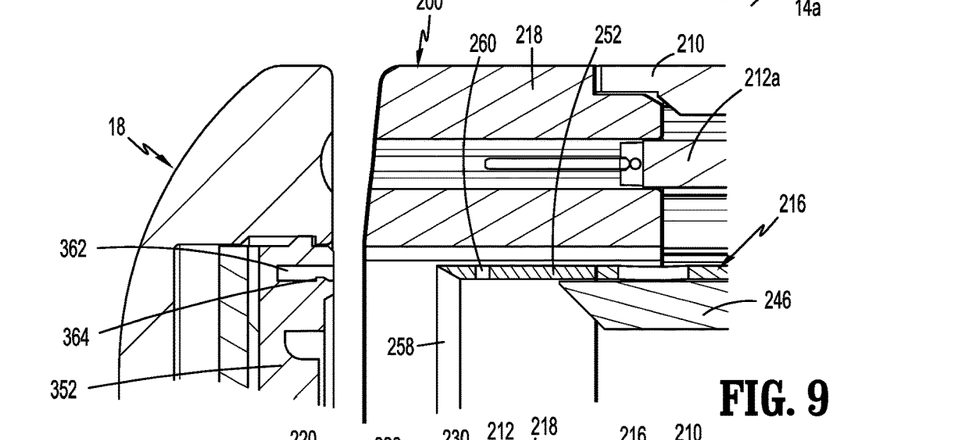
FIG. 9 is a side, cross-sectional, partial cutaway view of an alternate version of the tool assembly shown in FIG. 1 in a clamped, pre-fired position.

FIG. 9 illustrates the reload assembly 200 with the staple pushing member 212a and the annular knife assembly 216, including the distal knife portion 252, in a retracted position. In this position, the fingers 230 of the staple pushing member 212a are spaced proximally of the staples 220 within the staple pockets 226 of the staple cartridge 218. In addition, the annular knife assembly 216 is recessed within the shell housing 210 such that the cutting edge 258 of the distal knife portion 252 is shielded by the shell housing 210. As illustrated, the longitudinal extensions 246 of the knife carrier 214 extend along the proximal and distal knife portions 250 and 252 respectively to maintain alignment between the proximal and distal knife portions 250 and 252.

Figure 10:
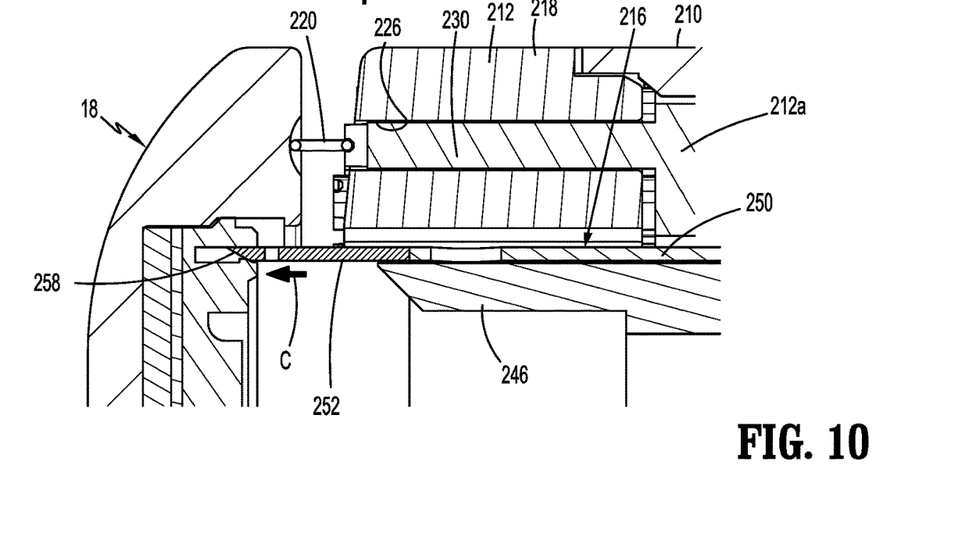
FIG. 10 is a side, cross-sectional, partial cutaway view of the tool assembly shown in FIG. 9 in the clamped position as the knife is advanced to cut tissue and the tool assembly is fired.

FIG. 10 illustrates the reload assembly 200 as the staple pushing member 212a and the knife carrier 214 and knife assembly 216 are moved towards their advanced positions. As the staple pushing member 212a moves towards its advanced position, the fingers 230 of the staple pushing member 212a move through the staple pockets 226 of the staple cartridge 218 to eject the staples 220 from the staple cartridge 218. In addition, the knife carrier 214 advances to advance the knife assembly 216 in the direction indicated by arrow "C" to move the distal knife portion 252 of the knife assembly 216 into the bore 262 formed in the compliant cut ring 252 of the cut ring assembly 250. As the cutting edge 258 of the distal knife portion 252 of the knife assembly 216 enters the bore 262, the cutting edge 258 engages and passes over the retention member 264.

Figure 11:
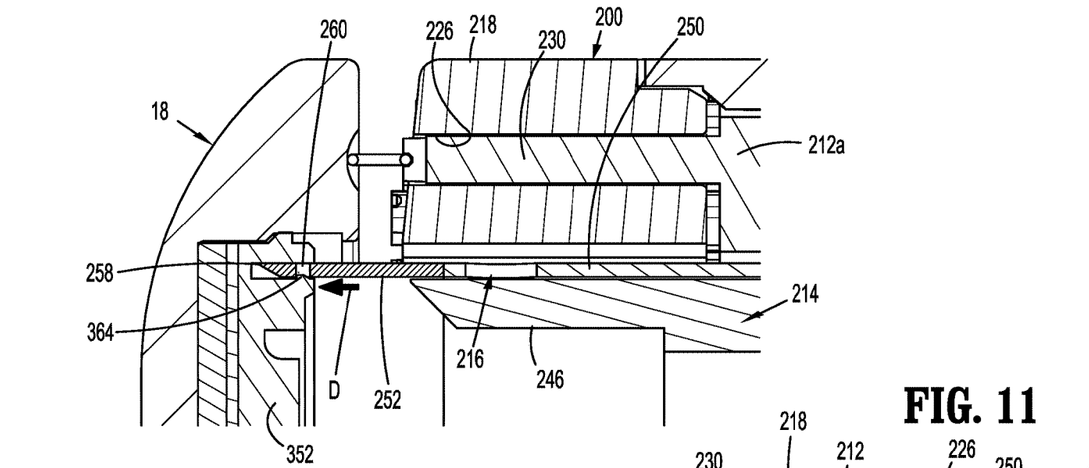
FIG. 11 is a side, cross-sectional, partial cutaway view of the tool assembly shown in FIG. 9 in the clamped position with the knife advanced to cut tissue and the tool assembly fired.

FIG. 11 illustrates the knife carrier 214 and the knife assembly 216 in their advanced positions. In the advanced position of the knife assembly 216, the distal knife portion 252 is positioned such that the retention member 364 of the compliant cut ring 352 is received in the opening 260 in the distal knife portion 252 to retain the distal knife portion 252 in its advanced position. When the knife carrier 214 is returned to its retracted position with the proximal knife portion 250 attached to the knife carrier 214, the distal knife portion 252 remains attached to the compliant cut ring 352 to retain the cutting edge 258 of the distal knife portion 252 shielded within the bore 364 of the compliant cut ring 352.

Figure 12:
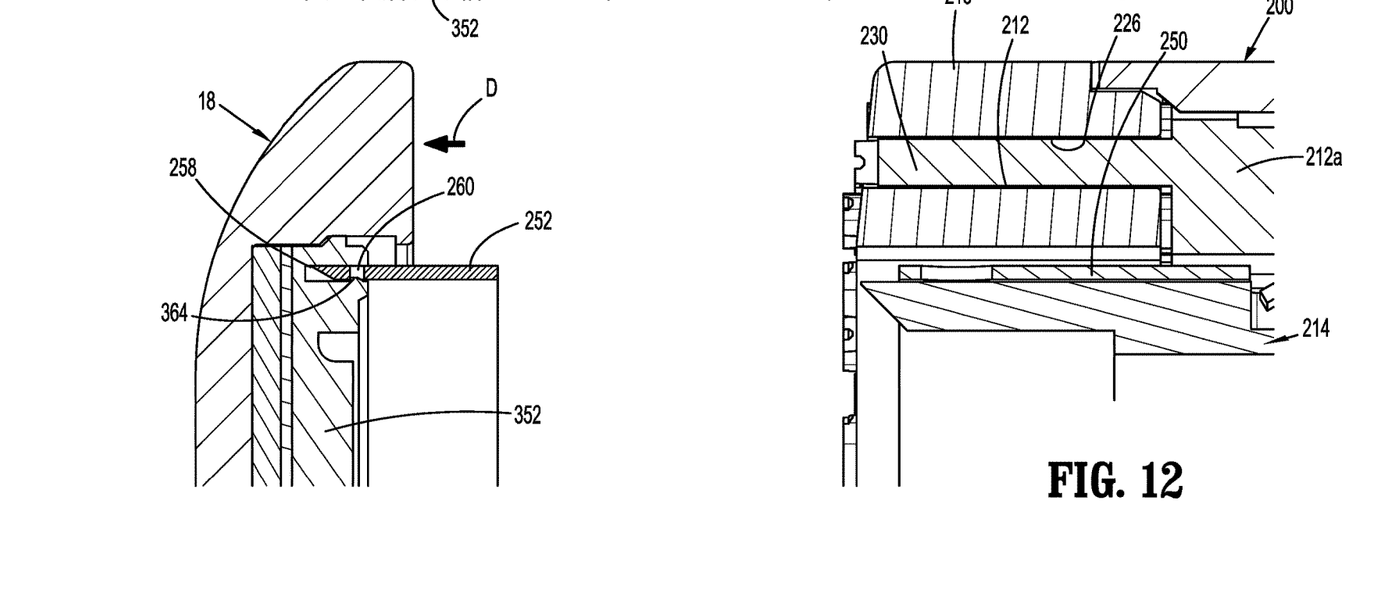
FIG. 12 is a side, cross-sectional, partial cutaway view of the tool assembly shown in FIG. 11 in the unclamped position with the knife fractured and retracted.

FIG. 12 the reload assembly 200 and the anvil assembly 18 in a post-fired unclamped position. In this position, the staple actuator (not shown) and the knife carrier 214 are returned in the direction indicated by arrows "D" to their retracted positions. Since the staple pushing member 212a and the staple actuator (not shown) are only in abutting relation, the staple pushing member 212a remains in an advanced position with the fingers 230 received within the staple pockets 226 of the staple cartridge 218. Similarly, since the proximal knife portion 250 is only in abutting relation to the distal knife portion 252 of the knife assembly 216, the distal knife portion 252 remains in its advanced position engaged with the compliant cut ring 352 when the knife carrier 214 and proximal knife portion 250 return to their retracted position. It is noted that receipt of the retention member 364 of the compliant cut ring 352 within the opening 260 of the distal knife portion 252 retains the distal knife portion 252 in its advanced position with the annular cutting edge 258 of the distal knife portion 252 of the knife assembly 216 buried within and shielded by the compliant cut ring 352.

Although not illustrated herein, it is envisioned that the knife assembly 116, 216 can be directly secured to the staple actuator 112, 212 such that the knife assembly 116, 216 is moved simultaneously with the staple actuator 112, 212 and the staple pushing member 112a, 212a. In such a device, the knife carrier 214 need not be included in the reload assembly 100, 200.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspects of the disclosure may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A reload assembly comprising:
a shell housing defining a cavity and having a proximal portion and a distal portion;
a staple cartridge supported on the distal portion of the shell housing, the staple cartridge supporting a plurality of staples;
a staple pushing member movable within the shell housing between an advanced position and a retracted position to eject the plurality of staples from the staple cartridge, the staple pushing member defining a longitudinal bore;
a knife carrier supported within the longitudinal bore of the staple pushing member, the knife carrier being movable between retracted and advanced positions within the shell housing; and
a knife assembly including a distal knife portion and a proximal knife portion, the proximal knife portion secured to the knife carrier and movable with the knife carrier as the knife carrier is moved between the retracted and advanced positions, the distal knife portion in abutting relation with the proximal knife portion, wherein the knife carrier and the proximal knife portion are movable from the advanced position to the retracted position independently of the distal knife portion.

2. The reload assembly of claim 1, wherein the proximal and distal knife portions are annular.

3. The reload assembly of claim 2, wherein the proximal knife portion has a first diameter and the distal knife portion has a second diameter equal to the first diameter.

4. The reload assembly of claim 1, wherein the distal knife portion includes an annular cutting edge.

5. The reload assembly of claim 1, wherein the knife carrier includes a distal body portion, the distal body portion having distal extensions that extend along the knife assembly to maintain alignment between the proximal and distal knife portions.

6. The reload assembly of claim 1, wherein the distal knife portion includes an opening positioned adjacent and proximal to the annular cutting edge, the opening being dimensioned to receive a retention member of an anvil assembly.

7. The reload assembly of claim 1, further including a coupling mechanism adapted to secure the reload assembly to a stapling device.

8. A stapling device comprising:
a handle assembly;
an adaptor assembly extending from the handle assembly, the adaptor assembly having a distal end portion;
an anvil assembly including a cut ring; and
a reload assembly supported on the distal end portion of the adaptor assembly, the reload assembly including:
a shell housing defining a cavity and having a proximal portion and a distal portion;
a staple cartridge supported on the distal portion of the shell housing, the staple cartridge supporting a plurality of staples;
a staple pushing member movable within the shell housing between an advanced position and a retracted position to eject the plurality of staples from the staple cartridge, the staple pushing member defining a longitudinal bore;
a knife carrier supported within the longitudinal bore of the staple pushing member, the knife carrier movable between retracted and advanced positions within the shell housing; and
a knife assembly including a distal knife portion and a proximal knife portion, the proximal knife portion secured to the knife carrier and movable with the knife carrier between the retracted and advanced positions, the distal knife portion positioned in abutting relation with the proximal knife portion such that movement of the proximal knife portion to the advanced position moves the distal knife portion to the advanced position, wherein the knife carrier and the proximal knife portion are movable from the advanced position to the retracted position independently of the distal knife portion.

9. The stapling device of claim 8, wherein the proximal and distal knife portions are annular.

10. The stapling device of claim 8, wherein the proximal knife portion has a first diameter and the distal knife portion has a second diameter equal to the first diameter.

11. The stapling device of claim 8, wherein the distal knife portion includes an annular cutting edge.

12. The stapling device of claim 8, wherein the knife carrier includes a distal body portion, the distal body portion including distal extensions that extend along the knife assembly to maintain alignment between the proximal and distal knife portions.

13. The stapling device of claim 8, wherein the distal knife portion includes an opening positioned adjacent and proximal to the annular cutting edge of the distal knife portion, and the cut ring defines a bore and includes a retention member extending into the bore, the distal knife portion received within the bore when the distal knife portion of the knife assembly is in its advanced position, the retention member received within the opening when the distal knife portion is in an advanced position to retain the distal knife portion in the advanced position.

14. The stapling device of claim 8, wherein the reload assembly further includes a coupling for securing the reload assembly to the adaptor assembly.

15. A reload assembly comprising:
a shell housing defining a cavity and having a proximal portion and a distal portion;
a staple cartridge supported on the distal portion of the shell housing, the staple cartridge supporting a plurality of staples;
a staple pushing member movable within the shell housing between an advanced position and a retracted position to eject the plurality of staples from the staple cartridge, the staple pushing member defining a longitudinal bore; and
a knife assembly including a distal knife portion; and a knife carrier secured to the proximal knife portion and a proximal knife portion, the distal knife portion in abutting relation with the proximal knife portion, wherein the proximal knife portion is movable from an advanced position to a retracted position independently of the distal knife portion.

16. The reload assembly of claim 15, wherein the distal knife portion includes an annular cutting edge.

17. The reload assembly of claim 15, wherein the knife carrier includes a distal body portion including distal extensions that extend along the knife assembly to maintain alignment between the proximal and distal knife portions.

18. The reload assembly of claim 15, wherein the proximal and distal knife portions are annular.

19. The reload assembly of claim 15, wherein the proximal knife portion has a first diameter and the distal knife portion has a second diameter equal to the first diameter.

20. The reload assembly of claim 15, wherein the distal knife portion includes an opening positioned adjacent and proximal to the annular cutting edge, the opening being dimensioned to receive a retention member of an anvil assembly.

21. A stapling device comprising:
a handle assembly;
an adaptor assembly extending from the handle assembly, the adaptor assembly having a distal end portion;
an anvil assembly including a cut ring; and
a reload assembly including:
a shell housing defining a cavity and having a proximal portion and a distal portion;
a staple cartridge supported on the distal portion of the shell housing, the staple cartridge supporting a plurality of staples;
a staple pushing member movable within the shell housing between an advanced position and a retracted position to eject the plurality of staples from the staple cartridge, the staple pushing member defining a longitudinal bore; and
a knife assembly including a distal knife portion and a proximal knife portion, the distal knife portion in abutting relation with the proximal knife portion, the knife assembly movable from a retracted position to an advanced position to move the distal knife portion into engagement with the cut ring of the anvil assembly, wherein the proximal knife portion is movable from the advanced position back to the retracted position independently of the distal knife portion such that the distal knife portion remains engaged with the cut ring of the anvil assembly; and
a knife carrier secured to the proximal knife portion.

* * * * *